Figure 1:
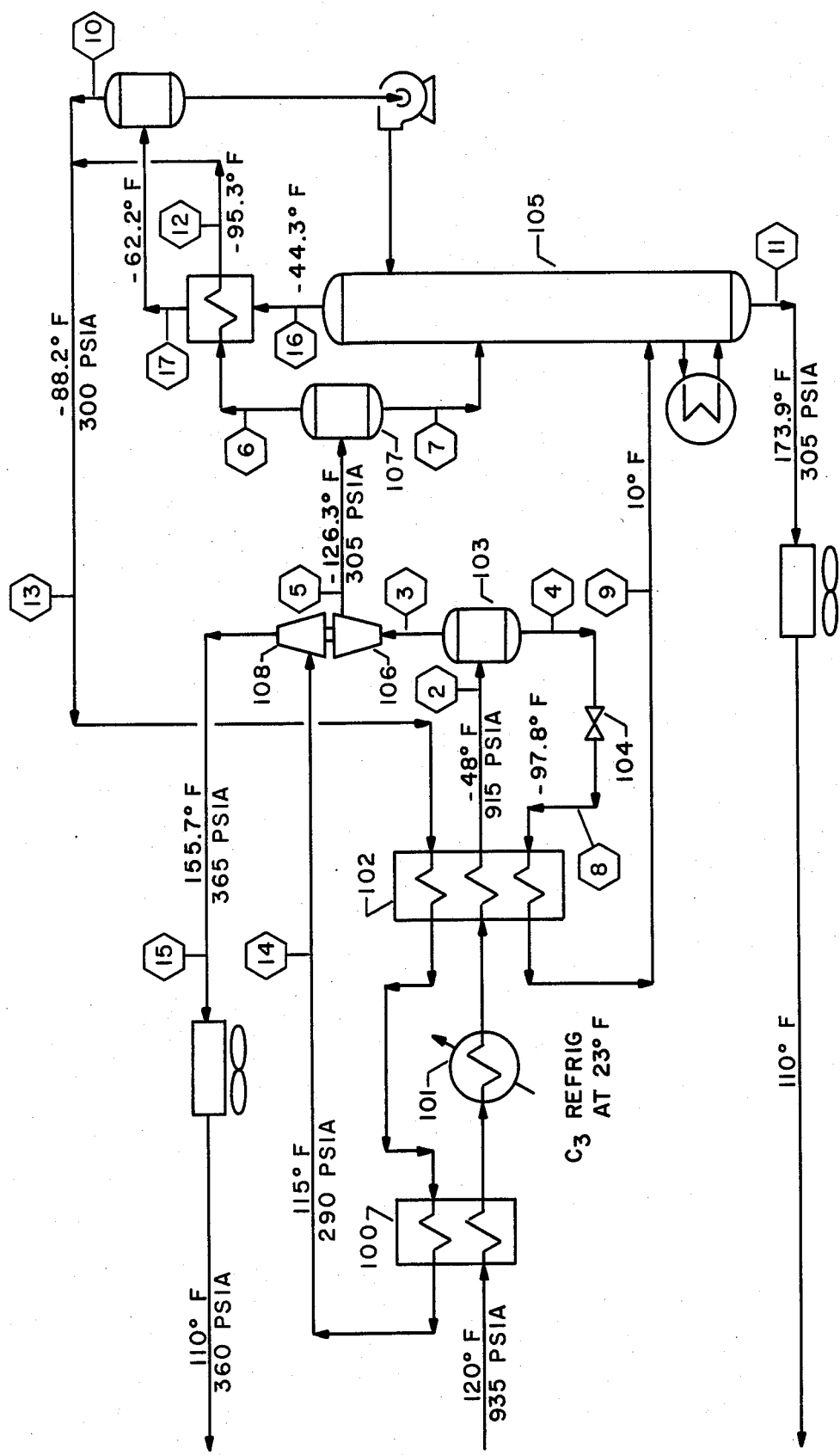

United States Patent [19]

Buck

[11] Patent Number: 4,617,039
[45] Date of Patent: Oct. 14, 1986

[54] SEPARATING HYDROCARBON GASES
[75] Inventor: Loren L. Buck, Tulsa, Okla.
[73] Assignee: Pro-Quip Corporation, Tulsa, Okla.
[21] Appl. No.: 673,039
[22] Filed: Nov. 19, 1984
[51] Int. Cl.[4] .................................................. F25J 3/02
[52] U.S. Cl. .......................................... 62/26; 62/28;
62/30; 62/31; 62/34; 62/39
[58] Field of Search ...................................... 62/23–28,
62/38, 39, 29, 30, 31, 34

[56] References Cited
U.S. PATENT DOCUMENTS
3,675,435 7/1972 Jackson et al. ..................... 62/39
4,251,249 2/1981 Gulsby .

OTHER PUBLICATIONS
Flow Plan Drawing, Job No. 82-1076 (The Pro-Quip Corporation).

Primary Examiner—Frank Sever
Attorney, Agent, or Firm—Brumbaugh, Graves, Donohue & Raymond

[57] ABSTRACT

The present invention relates to a process for separating a hydrocarbon gas into a fraction containing a predominant portion of the ethane and lighter components and a fraction containing a predominant portion of the $C_3$ and heavier components in which process the feed gas is treated in one or more heat exchange, and expansion steps; partly condensed feed gas is directed into a separator wherein a first residue vapor is separated from a $C_3$-containing liquid; and $C_3$-containing liquids, at substantially the pressure of separation, are directed into a distillation column wherein said liquid is separated into a second residue is separated to recover a $C_3$-containing product. The foregoing process is improved by cooling said second residue to partially condense it; directing the partially condensed second residue into said separator forming thereby a liquid portion and a vapor portion; intimately contacting at least the first residue vapor with at least the liquids portion of the partly condensed second residue in at least one contacting stage within said separator, and thereafter separating the vapors and liquids from said contacting stage; supplying the liquids thereby recovered to the distillation column as a top liquid feed thereto; and directing the vapors thereby recovered into heat exchange relation with said second residue from the fractionation column, and thereafter discharging said residue gases.

11 Claims, 4 Drawing Figures

4,617,039

SEPARATING HYDROCARBON GASES

BACKGROUND OF THE INVENTION

The present invention relates to a method and apparatus for the improved recovery of $C_3$ and heavier components from hydrocarbon gases.

In conventional processes for extracting propane and heavier components from hydrocarbon gases, the $C_3$ bearing gases are treated by a combination of expansion (or compression followed by expansion) heat exchange and refrigeration to obtain a partially condensed stream which is collected in a feed separator having a pressure typically in the order of 50 to 300 psia and a temperature in the order of $-50°$ to $-200°$ F. These conditions of course can vary substantially, depending on the pressure and temperature conditions necessary to achieve partial condensation for a particular gas, and the pressure and temperature at which the feed is available to the process. The liquid resulting from partial condensation is supplied to a fractionation column called a "deethanizer" as a mid-column feed while the vapor from the feed separator is used to generate reflux by partially condensing the overhead vapors from the deethanizer through appropriate heat exchange means. In a typical system the deethanizer column will operate at a pressure substantially equal to that of the deethanizer feed separator (possibly allowing for a small pressure drop as the partially condensed liquid passes from the separator to the deethanizer) and the deethanizer overhead vapors leave at a temperature in the order of $-20°$ to $-70°$ F. The heat exchange of these overhead vapors against the residue vapors from the low pressure separator provides partial condensate which is used as a reflux to the deethanizer column.

Pre-cooling of the gas before it is expanded to the deethanizer pressure will commonly result in formation of a high-pressure condensate. To avoid damage to the expander, the high pressure condensate, if it forms, is usually separated, separately expanded through a Joule-Thomson valve and used as a further feed to the mid-portion of the deethanizer column. Refrigeration in such a process is sometimes entirely generated by work expansion of the vapors remaining after partial condensation of the high pressure gas to the column operating pressure. Other processes may include external refrigeration of the high pressure gases to provide some of the required cooling.

When processing natural gas, feed is typically available at line pressure, of 900-1000 psia. In such case expansion to a pressure in the order of 250-300 psia is common. In an alternate process, facilities may be designed to extract propane or propylene from refinery gases. Refinery gases commonly are available a pressure of 150 psia-250 psia. In this case, at the convenience of the process designer, the deethanizer may be designed to operate at a pressure below the pressure of the refinery gas which is available, i.e., perhaps 50-100 psia, so that work expansion can be used to supply refrigeration to the process. This will result in lower deethanizer temperatures and will increase potential heat leakage and other engineering problems associated with cryogenic temperatures. It is also possible in this case to compress the refinery gas to a higher pressure so that it may be thereafter expanded in a work-expansion machine to afford refrigeration to the overall process.

A typical flow plan of a process for separating $C_3$ and heavier hydrocarbons from a gas stream is illustrated in U.S. Pat. No. 4,251,249 to Jerry G. Gulsby.

DESCRIPTION OF THE INVENTION

The present invention provides an improved process for recovering $C_3$ and heavier components from hydrocarbon-bearing gases. In the improved process of the present invention the overhead vapor from the deethanizer column is partly condensed and then at least the liquid condensate is combined with at least the vapor from the partially condensed feed gases described above in the deethanizer feed separator which, in the present invention, also acts as an absorber. The feed separator/absorber is designed to afford one or more contacting stages. Usually such stages are assumed for design purposes to be equilibrium stages, but in practice this need not be so. Vapor from the feed separator/absorber passes in heat exchange relation to the overhead from the deethanizer, thereby providing partial condensation of that stream, and liquid from the feed separator/absorber is supplied to the deethanizer as an upper or top liquid feed to the column.

If the separator/absorber contains an absorption section, such as packing, or one or more fractionation trays, these stages will be assumed to correspond to a suitable number of theoretical separation stages. Our calculations have shown benefits with as few as one theoretical stage, and greater benefits as the number of theoretical stages is increased. We believe that benefits can be realized even with the equivalent of a fractional theoretical stage. The partially condensed deethanizer overhead is supplied above this section, and the liquid portion of it passes downward through the absorption section. The partially condensed feed stream is usually supplied below the absorption section, so that the vapor portion of it passes upwardly through it in countercurrent contact with the liquids from the partially condensed deethanizer overhead. The rising vapor joins the vapors which separate from partially condensed deethanizer overhead above the absorption section, to form a combined residue stream.

While described above with respect to a preferred embodiment in which overhead vapors are condensed and used to absorb valuable propane, propylene, etc. from the expander outlet vapors, we point out that the present invention is not limited to this exact embodiment. Advantages can be realized, for instance, by treating only a part of the expander outlet vapor in this manner, or using only part of the overhead condensate as an absorbent in cases where other design considerations indicate that portions of the expander outlet or overhead condensate should bypass the feed separator/absorber. We also point out that the feed separator/absorber can be constructed as either a separate vessel, or as a section of the deethanizer column.

In the practice of this invention there will necessarily be a slight pressure difference between the separator/absorber and the deethanizer which must be taken into account. If the overhead vapors pass through the condenser and into the separator without any boost in pressure, the feed separator/absorber will assume an operating pressure slightly below the operating pressure of the deethanizer. In this case the liquid feed withdrawn from the separator/absorber can be pumped to its feed position in the deethanizer. An alternative is to provide a booster blower in the vapor line to raise the operating pressure in the overhead condenser and separator/absorber sufficiently so that the liquid feed can be supplied to the deethanizer without pumping. Still another alternate is to mount the feed separator/absorber at a sufficient elevation relative to the feed position of the liquid withdrawn therefrom that the hydrostatic head of the liquid will overcome the pressure difference.

In still another alternate, all or a part of the partially condensed deethanizer overhead and all or part of the partially condensed feed can be combined, such as in the pipe line joining the expander output to the feed separator/absorber and if thoroughly intermingled, the liquids and vapors will mix together and separate in accordance with a relative volatility of the various components of the total combined streams. In this embodiment the vapor-liquid mixture from the overhead condenser can be used without separation, or the liquid powder thereof may be separated. Such co-mingling is considered for purposed of this invention as a contacting stage.

In still another variation of the foregoing, the partially condensed overhead vapors can be separated, and the all or a part of the separated liquid supplied to the separator/absorber or mixed with the vapors fed thereto.

The present invention provides improved recovery of propane or propylene per amount of horsepower input required to operate the process. An improvement in operating horsepower required for operating a deethanizer process may appear either in the form of reduced power requirements for external refrigeration, reduced power requirements for compression or recompression, or both. Alternatively, if desired, increased $C_3$ recovery can be obtained for a fixed power input.

The present invention can be better understood by the following examples of its operation. These examples represent computer simulations of anticipated process conditions when following the prior art (base case) and when employing the present invention to treat a natural gas (Examples 1 and 2) and also using the present invention to treat a refinery gas (Example 3).

Base Case

For purposes of a base case, a calculation was made on a natural gas received into the processing plant at a temperature of 120° F. and a pressure of 935 psia. FIG. 1 shows a flow diagram of the process utilized as a base case.

Incoming feed gas is partly condensed to a temperature of −48° F. in heat exchangers 100, 101, 102 with residue gas (stream 13), external propane refrigeration, and flashed vapor-liquid mixture resulting from expansion of the partial condensate (stream 8) collected in high-pressure separator 103. Allowing for pressure drop through heat exchangers 100, 101 and 102 of the initial gas cooling section, high pressure separator 103 is estimated to operate at a temperature of '1 48° F. and a pressure of 915 psia. At this condition, approximately 15 percent of the hypothetical incoming gas is condensed.

The resulting partial condensate is separated in high pressure separator 103. The liquids (stream 4) are flashed and partially vaporized by passage through a Joule-Thomson expansion (valve 104) to a temperature of about −98° F. (stream 8), and pass into heat exchange relation with partially cooled feed gas in exchanger 102, thereby warming the stream 8 to a temperature of about 10° F. (stream 9) and further vaporizing it. Stream 9 is supplied to deethanizer 105 at a mid column feed position.

Vapors from the high pressure separator (stream 3) are expanded in a turbo-expander 106 to a pressure of about 305 psia at a temperature of about −126° F. (stream 5). When expanded in this fashion, approximately 12 percent of the original high pressure vapor stream 3 condenses. Stream 5 is collected in a low pressure feed separator 107 wherein the vapor and liquid are separated. The liquids from the separator (stream 7) are supplied to deethanizer 105 at the third tray. The deethanizer is operated at a pressure of approximately 305 psia. The bottoms product from the deethanizer (stream 11) at a temperature of 174° F. contains approximately 95.6 percent of the propane that was in the feed, and approximately 99.6 percent of the butane.

Overhead vapor from the deethanizer (stream 16), at a temperature of −44° F., is directed into heat-exchange relation with the vapors from the expander outlet (stream 6). This heat-exchange warms the expander outlet vapors to about −95° F. (stream 12) and cools the deethanizer overhead to approximately −62° F. (stream 17). This cooling condenses approximately 18.7 percent of the overhead vapor, which is returned to the deethanizer at stage 1 as reflux. The vapors remaining (stream 10) after condensation of reflux from the deethanizer overhead are combined with residue vapors from the low pressure feed separator, stream 12, to form the residue gas from the process stream 13, at a pressure of 300 psia and a temperature of −88° F.

Residue stream 13, passes through heat exchangers 102 and 100 to extract the cooling values contained in it by heat exchange against incoming feed gas. The warmed residue, stream 14, by now at a temperature of 115° F. and an estimated pressure of 290 psia, is partially recompressed in a booster compressor 108 driven by the turbo-expander 106 to a pressure of 365 psia (stream 15). After cooling, the residue gas reaches a temperature of 110° F. and a pressure of 360 psia. This gas can be further compressed to the original line pressure by a recompressor (not shown).

The following table sets forth the total flow rates, temperatures and pressures for the principal streams described above, together with the flow rates of methane, ethane, $C_3$ (propane and propylene), and $C_4$ (isobutane, butylene and normal butane) in each of these streams.

TABLE I

| | FEED | STREAM 3 | STREAM 4 | STREAM 6 | STREAM 7 | STREAM 10 | STREAM 11 | STREAM 13 |
|---|---|---|---|---|---|---|---|---|
| | | | | BASE CASE | | | | |
| Total Moles/hr | 6094 | 5177 | 917 | 4575 | 602 | 1207 | 311 | 5782 |
| Pressure, psia | 935 | 915 | 915 | 305 | 305 | 305 | 305 | 300 |
| Temperature | 120° | −48° | −48° | −126° | −126° | −62° | 174° | −88° |
| $C_1$ (Moles/hr) | 5297 | 4734 | 563 | 4404 | 330 | 893 | nil | 5297 |
| $C_2$ (Moles/hr) | 441 | 298 | 143 | 127 | 171 | 311 | 3 | 438 |
| $C_3$ (Moles/hr) | 194 | 84 | 110 | 7 | 77 | 2 | 185 | 9 |
| $C_4$ (Moles/hr) | 89 | 21 | 68 | nil | 21 | nil | 89 | nil |

TABLE I-continued

| | FEED | STREAM 3 | STREAM 4 | BASE CASE STREAM 6 | STREAM 7 | STREAM 10 | STREAM 11 | STREAM 13 |
|---|---|---|---|---|---|---|---|---|
| $C_3$ Recovery: | | | | 95.61% | | | | |
| $C_4$ Recovery: | | | | 99.63% | | | | |
| Expander Horsepower: | | | | 837 @82% | | | | |
| Booster Horsepower: | | | | 816 @72% | | | | |
| External Refrig: | | | | 1.94 MMBtu | | | @23° F. | |
| Horsepower: | | | | 257 @75% | | | | |

EXAMPLE 1

Figure 2:
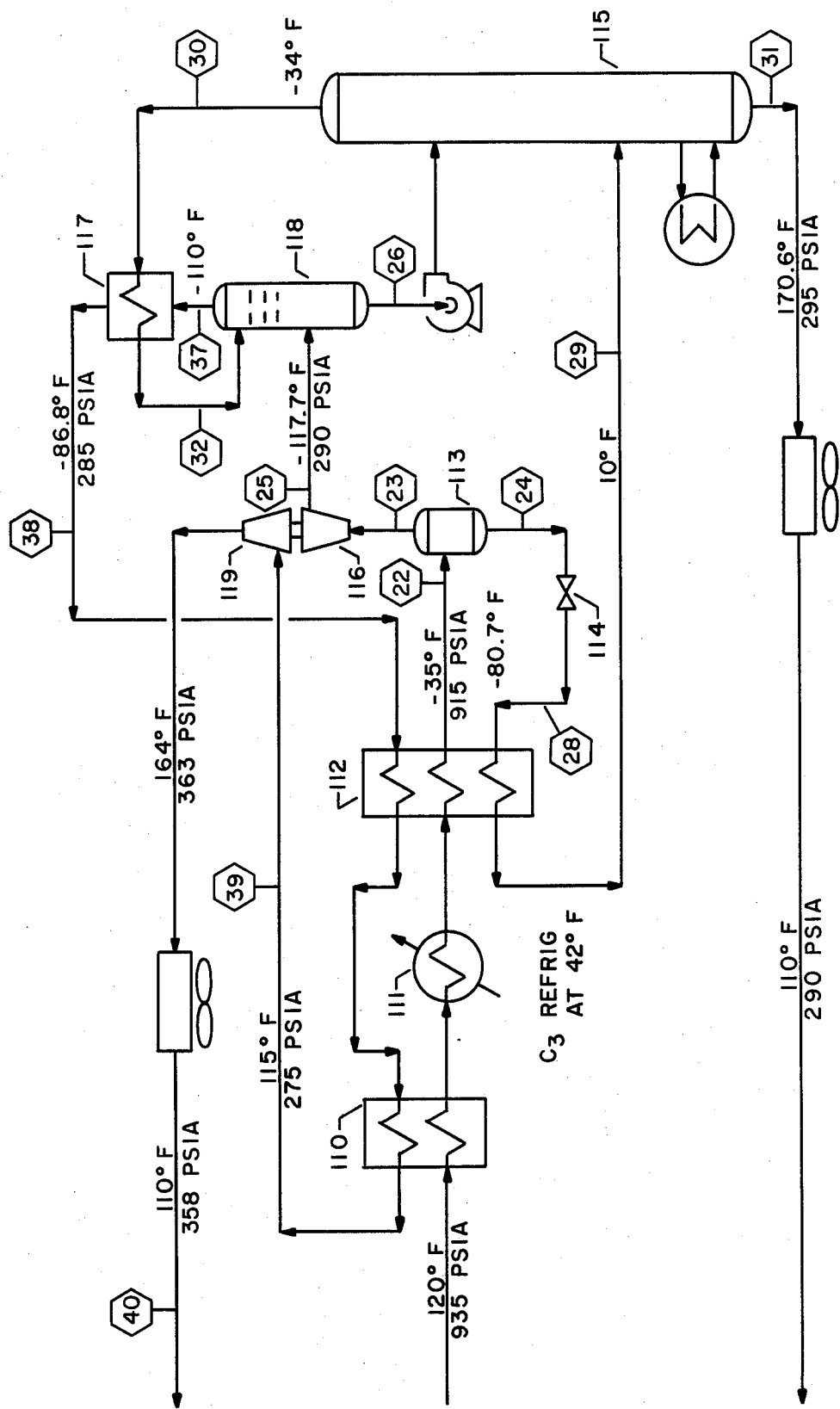

The present invention is illustrated by a simulation of the process illustrated in FIG. 2. To facilitate comparison of the results of simulating the process of the present invention with the simulation of the prior art illustrated in the base case the simulation was carried out using the same assumed feedstock and feed conditions as were employed for purposes of the base case.

In the process of the present invention, incoming feed gas at 120° F. and 935 psia is cooled to approximately −35° F. in heat exchangers 110, 111 and 112. To allow for pressure drop through the heat exchange circuits it was assumed that the pressure at the high pressure separator had dropped to approximately 915 psia. Under these conditions approximately 10 percent of the incoming gas condenses. The partly condensed feed gas, stream 22, is separated in a high pressure separator 113 into vapor and liquid streams 23 and 24. The liquid, stream 24, is flash expanded in Joule-Thomson valve 114 to 315 psia, at which pressure it reaches a temperature of about −81° F. (stream 28). After heating stream 28 to +10° F. in heat exchanger 112, it is supplied (stream 29) to a mid column feed position in deethanizer 115.

Overhead vapor (stream 23) from the high pressure separator flows to a turbo-expander 116 wherein the vapors are expanded to approximately 290 psia, at which pressure the expanded vapors reach a temperature of approximately −118° F. The vapors from the expander (stream 25) flow to the lower portion of a feed separator/absorber 118 in accordance with the present invention. Liquids from the feed separator/absorber, stream 26, are withdrawn and supplied as top liquid feed to the deethanizer column.

The overhead vapor from the feed separator/absorber, stream 37, at −110° F., passes into heat exchange relationship with the overhead vapor from the deethanizer column originally at −34° F. (heat exchanger 117). In heat exchange 117 the overhead vapor from the feed separator is warmed to approximately −87° F. (stream 38) while the deethanizer overhead is cooled to approximately −67° F., at which temperature it is partially condensed (stream 32). The partial condensate which results from this heat exchange, stream 32, is supplied at the top of the feed separator/absorber 118 in accordance with the present invention.

Residue vapors from heat exchanger 117, now heated to approximately −87° F., thereafter pass in heat exchange relation with incoming feed and are heated to approximately 115° F. (stream 39). Allowing for pressure drop through the various heat exchangers the pressure of the residue gas was assumed at this point to be approximately at 275 psia. It is partly recompressed in a booster compressor 119, connected by a common shaft to the expansion turbine, and air-cooled, resulting in a residue gas (stream 40) of approximately 358 psia at 110° F.

As in the base case, this residue gas, if it is to be returned to the natural gas pipeline, must be recompressed to approximately 935 psia, the line pressure. Recompression horsepower of this simulation of the present invention, when compared with the recompression horsepower of the base case described above, will be substantially the same.

As can be seen in accordance with the present invention at least the vapor phase of the expander outlet, or a substantial portion thereof, is brought into a vapor/liquid contact relationship with the condensate from the partially condensed recycle vapors leaving the deethanizer column. This vapor/liquid contact can take place in the feed separator/absorber of the present invention. If it is desired to limit the contact to a single contacting stage, it can take place in the piping between the turbo-expander and the feed separator/absorbor, with the co-mingled vapors and liquids passing into the separator, where phase separation occurs. In the present simulation this feed separator/absorber was assumed to be a packed section in the upper portion of the feed separator/absorber which was calculated as equivalent to approximately three distillation stages. Vapors from the expander outlet rose through this packed section, while liquid condensed in the deethanizer overhead passed downwardly in counter-current vapor/liquid contact with the rising expander outlet vapors. The liquids thereby absorb additional propane from the feed which is returned to the deethanizer column as the top liquid feed, or reflux, along with the expander outlet liquids. The expander outlet vapors, after passing through the scrubbing section, combined with the uncondensed vapors in the deethanizer overhead to form the residue gas stream 37.

In both the base case, and the present invention, losses of propane into the residue gas stream are governed by the equilibrium temperature of the residue gas leaving the expander outlet separator. Any means for further reduction of such final vapor-liquid equilibrium temperature will result in increased product recovery. Conventionally, as in the base case, this is the temperature achieved through expansion of the gas stream through the expander or J-T valve, where as in the proposed scheme, the final point of equilibrium is the uppermost liquid-vapor contact stage in the outlet separator. The condensed liquid stream introduced at this point serves as an absorbent which permits $C_3+$ recovery at a warmer equilibrium temperature, or increased $C_3+$ recovery if a lower temperature is maintained. As an absorbent, this stream condenses heavier components in stage to stage contact with the gas stream to permit their final recovery as product, while undesired light components such as methane and ethane tend to remain as vapor.

In many cases, depending on the amount of condensate which results from partially condensing the depropanizer overhead, a refrigeration effect can be obtained. The occurrence of this refrigeration effect was most surprising. Analysis of the printouts showed that temperatures in the separator/absorber are significantly colder than the expander outlet temperature. This appears to be due to vapor-liquid equilibrium in the expander outlet vapor in relation to the vapor-liquid equilibrium in the bottom of the separator/absorber. The former is lean in methane relative to the descending liquid in the separator/absorber, so that as the expander outlet vapor rises it tends to volatilize light ends such as methane from the absorber liquid, thereby cooling the absorber liquid. As this further cooled vapor rises it cools the liquid falling through the separator/absorber, and leaves the top liquid stage colder than the temperature achieved at the expander outlet. In some cases the extent of this cooling is sufficient that the mixture of uncondensed deethanizer overhead and separator/absorber vapor leaving the separator/absorber will also be colder than the expander inlet. For instance, in Example 3 (infra) the overhead vapor from top liquid stage of the separator/absorber is almost 22° F. colder than the expander outlet. In some cases this refrigeration effect will occur, but will be obscured as the refrigerated streams mix with warmer expander outlet liquids and vapors from the deethanizer overhead condenser. For instance in Example 1, the top stage vapors in the separator/absorber are estimated to be −119° F., however the mixture of the vapor in stream 32 (at −67°) which combines the absorber overhead vapors to form stream 17 is estimated to be about −110° F. In Example 2 (infra), both of the overall vapor and liquid streams leaving the separator/absorber (i.e. streams 57 and 56 in FIG. 3) are warmer than the expander outlet (stream 43); however the computer simulation discloses that the top liquid tray in the separator/absorber actually reaches a temperature of −114° F., over 3° F. colder than the temperature of the expander outlet.

At a fixed level of product recovery, incorporation of the proposed scheme permits operation of the expander, or J-T, outlet at a higher temperature. This, in turn, will permit either a lower pressure differential across the expander, or an increase in the temperature at the inlet to the expander, or both. The ultimate consequence is a reduction in energy required for compression of inlet gas, residue gas, or refrigerant.

The present invention surprisingly operates significantly more efficiently than the process of the base case. As pointed out above, both the base case and the simulation of the present invention require substantially the same recompression horsepower, and both were designed to produce substantially the same propane recovery. In the process of the present invention conditions were selected to yield an estimated propane recovery of 95.68%, which compared with the estimated propane recovery in the base case of 95.61%. However, there is a substantial difference in the external refrigeration which is required in accordance with the present invention. To achieve a high propane recovery in the base case, it was necessary to cool the feed gas to −48° F. In the present invention cooling to only −35° F. was required. Thus the present invention required only 132 horsepower of external refrigeration, whereas the base case required 257 horsepower of external refrigeration.

A more detailed summary of the principal streams in the simulation of the present invention is set forth in Table II.

TABLE II

SIMULATION OF THE INVENTION

| | Stream 23 | Stream 24 | Stream 26 | Stream 37 | Stream 30 | Stream 32 | Stream 38 |
|---|---|---|---|---|---|---|---|
| Total Moles/hr | 5489 | 605 | 746 | 5783 | 1039 | 312 | 5782 |
| Pressure, psia | 915 | 915 | 290 | 290 | 295 | 295 | 285 |
| Temperature, ° F. | −35 | −35 | −119 | −110 | −34 | −67 | −87 |
| $C_1$ (moles/hr) | 4966 | 331 | 345 | 5297 | 676 | nil | 5297 |
| $C_2$ (moles/hr) | 344 | 97 | 245 | 438 | 339 | 3 | 438 |
| $C_3$ (moles/hr) | 107 | 86 | 121 | 8 | 22 | 185 | 8 |
| $C_4$ (moles/hr) | 30 | 59 | 31 | nil | 1 | 89 | nil |

| | | |
|---|---|---|
| $C_3$ Recovery: | | 95.68% |
| $C_4$ Recovery: | | 99.86% |
| Expander Horsepower: | 1014 | 82.00% |
| Booster Horsepower: | 993 | 72.00% |
| External Refrigeration: | 1.363 mm Btu/Hr | 42° F. |
| Horsepower: | 132 | 75.00% |

EXAMPLE 2

The present invention may be employed in propane recovery processes where external refrigeration is omitted. When external refrigeration is omitted, the temperature approaches in the heat exchangers limit the available cooling which can be recovered from the residue gases. Accordingly, it is necessary under these circumstances that the high pressure separator operate at a higher temperature, and a lower propane recovery results.

Figure 3:
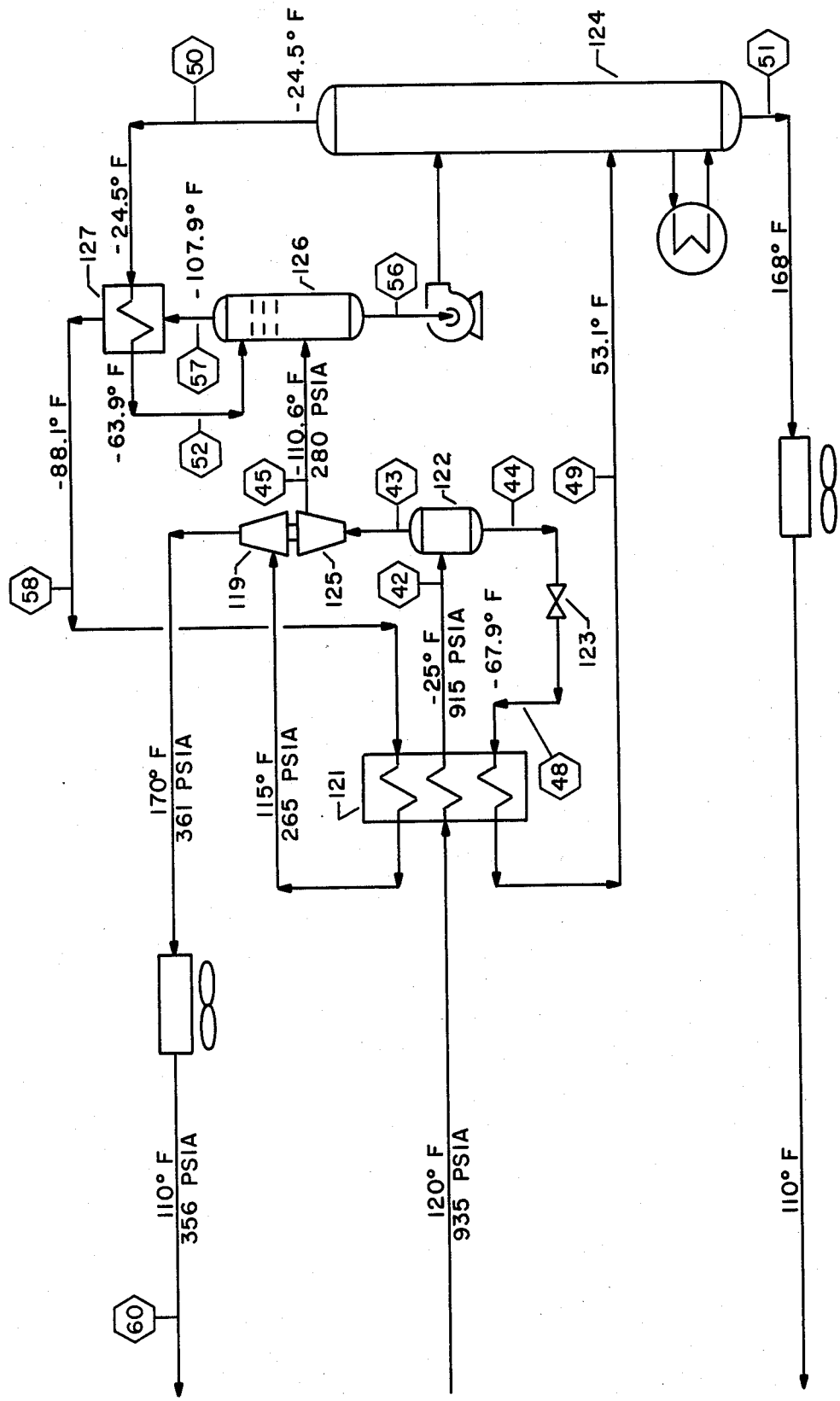

Illustrating such a process, reference may be had to FIG. 3. As shown in FIG. 3, incoming feed gas at 120° F. and 935 psia is cooled in heat exchanger 121 to a temperature of −25° F. (stream 42). Pressure at the high pressure separator 122 was assumed to be approximately 915 psia.

The liquids from the high pressure separator (stream 44) pass through a Joule-Thomson valve 123 wherein they are expanded to approximately −68° F. (stream 48), supply a portion of the cooling of the incoming feed gas, and thereafter are supplied (stream 49) to the deethanizer column 124 at a temperature of approximately 53° F. In this example the deethanizer was assumed to be operating at a pressure of 285 psia.

Vapors from the high pressure separator 122, stream 43, flow to a turbo-expander 125 wherein they are expanded to a pressure of approximately 280 psia and −111° F. (stream 45). The expander outlet vapors are supplied to the lower portion of the feed separator/absorber 126 in accordance with the present invention. Liquids from the separator/absorber (stream 56) is supplied as the top liquid feed and reflux to the deethanizer column.

The overhead vapor from the feed separator absorber at approximately −108° F. (stream 57) is used, as in the previous example, to partially condense the overhead vapor leaving the deethanizer (stream 50) in heat exchanger 127. In this partial condensation the overhead vapors from the deethanizer are cooled from −24° F. to approximately −64° F. (stream 52). Residue gas from the overhead condenser 127, at −88° F. (stream 58) passes into heat exchange relation with the incoming feed to supply additional cooling thereto, is recompressed in a booster compressor, and is air-cooled to yield a residue gas of 356 psia at 110° F. (stream 60).

The partially condensed overhead vapors from the deethanizer, stream 52, are introduced above the packed section in the feed separator/absorber in accordance with the present invention. The condensate which is contained in this stream passes downwardly through the packed section in counter-current contact with the upwardly rising uncondensed vapors from the turbo-expander 125. These liquids, after absorbing desirable components from the rising vapors combine with the condensate which is formed upon turbo-expansion to form the top liquid feed to the deethanizer (stream 56). The rising vapors, after they pass through the packed section, join the uncondensed vapors from the deethanizer overhead to form the residue stream 57.

In this simulation of the present invention, the absorber-feed separator was assumed to contain a packed section calculated as equivalent to approximately three theoretical distillation stages. The calculated propane recovery was approximately 92.65 percent. The recompression horsepower requirements would be similar to the recompression horsepower requirements of Example 1 or the base case, since the residue gas discharged to the recompressors is approximately at the same conditions.

A more detailed stream summary of the simulation of Example 2 is set forth in the following table.

exchanger to approximately 190 psia in high pressure separator 131. In this design, section C of exchanger 130 was assumed to be provided for the purpose of optional external refrigeration, although in this simulation no external refrigeration was included.

The liquid from the high pressure separator stream 61, passes through a Joule-Thomson valve 132, wherein it is expanded to about 54 psia, at which pressure reaches a temperature of −66° F. This expanded liquid is used to provide a portion of the cooling required for the incoming feed gas, in Section D of heat exchanger 130 and thereby heating it to a temperature of approximately −21° F., and thereafter is supplied as stream 64 to mid column position in fractionation column, 138.

The overhead vapors from the high pressure separator at −46° F., stream 62, pass through a turbo-expander, 133, and are expanded to approximately 53 psia, at which pressure the expanded vapors reached a temperature of approximately −117° F. The expanded vapor, stream 69, is supplied to the lower portion of feed separator/absorber, 134, in accordance with the present invention.

Liquids from the feed separator/absorber, at −117° F., are pumped, by pump 135, to supply the top liquid feed to the deethanizer column (stream 63). Overhead vapors from the feed separator/absorber, at −129° F., stream 66 pass into heat exchange relationship with overhead vapors at −61° F. from the deethanizer overhead (stream 65) in condenser 136. The deethanizer overhead is thereby cooled to approximately −122° F., partially condensed, and supplied to the feed separator/absorber 134 as the top liquid feed thereto. The partly warmed residue gas stream 70 leaving heat exchanger 136, at −80° F., passes through heat exchanger 130 whereby additional refrigeration value is extracted therefrom and the residue warmed to approximately 82° F. The residue is recompressed in a booster compressor 137 on a common shaft with a turbo-expander 133, to provide a residue gas (stream 68) at a temperature of 163° F. and 72 psia.

TABLE III

| SIMULATION OF THE INVENTION | | | | | | |
|---|---|---|---|---|---|---|
| Stream 43 | Stream 44 | Stream 56 | Stream 57 | Stream 50 | Stream 51 | Stream 58 |
| Total Moles/hr | 5653 | 441 | 628 | 5788 | 763 | 306 | 5788 |
| Pressure | 915 | 915 | 280 | 280 | 285 | 285 | 275 |
| Temperature | −25 | −25 | −111 | −108 | −25 | 168 | −88 |
| $C_1$ (moles/hr) | 5075 | 222 | 248 | 5297 | 470 | nil | 5297 |
| $C_2$ (moles/hr) | 371 | 70 | 199 | 438 | 266 | 3 | 438 |
| $C_3$ (moles/hr) | 126 | 68 | 135 | 14 | 24 | 180 | 14 |
| $C_4$ (moles/hr) | 38 | 51 | 39 | nil | 2 | 89 | nil |

EXAMPLE 3

Figure 4:
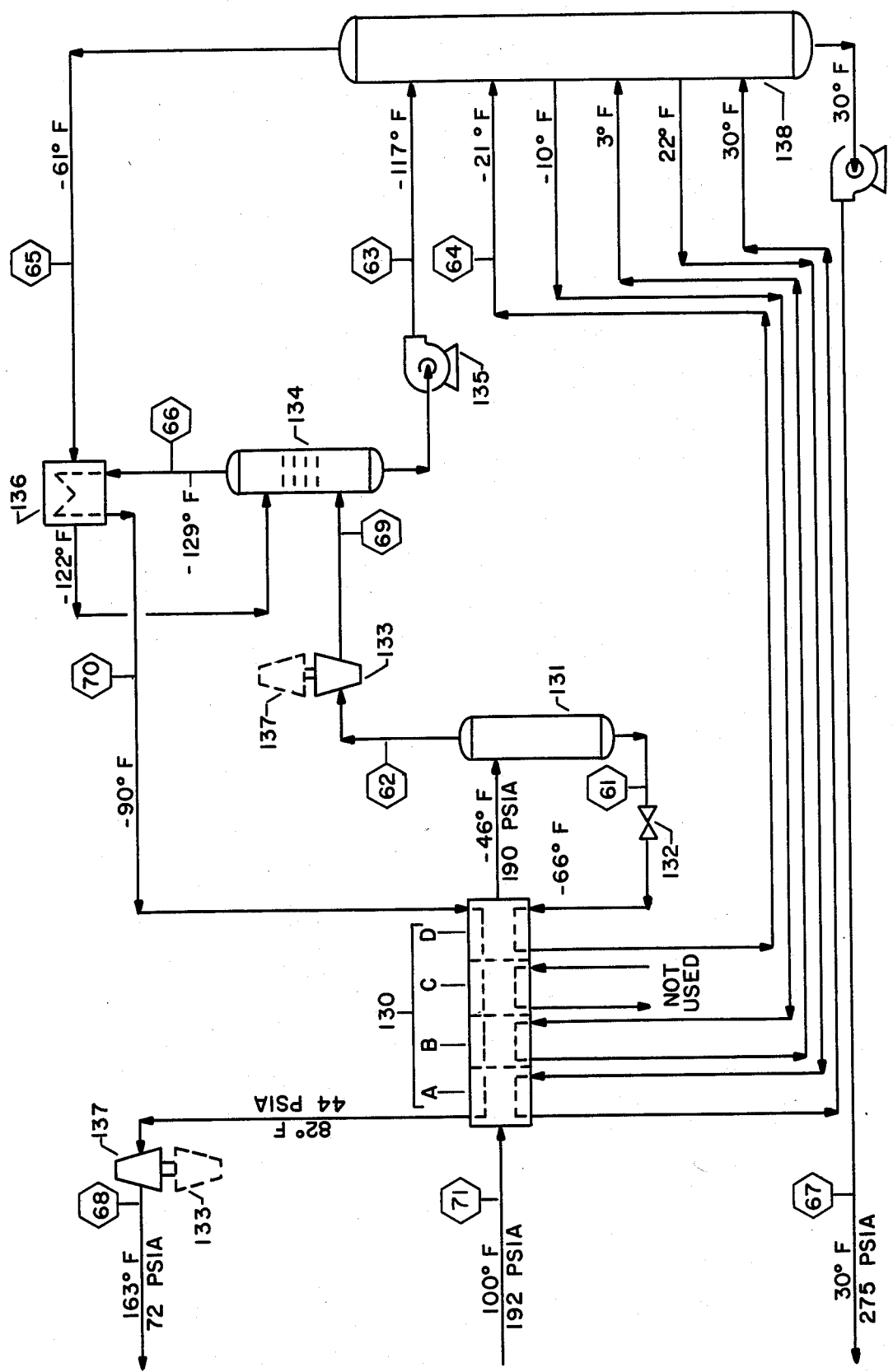

Examples 1 and 2 illustrated the application of the present invention to processing of a natural gas. As indicated at the outset, the present invention is also applicable to processing refinery gases for recovery of $C_3$ components, i.e., either propane and propylene. FIG. 4 illustrates the application of the present invention to such a situation.

In FIG. 4, a refinery gas (stream 71) is received into the process at a pressure of 192 psia and 100° F. The gas was cooled in sections A, B, C and D of Exchanger 130 to a temperature of −46° F. and it was assumed that the pressure had fallen as the gas passed through the heat In this simulation of the present invention, the feed separator/absorber, was calculated as fractionation section equivalent to four theoretical distillation stages.

The estimated recoveries which were obtained in the practice of the present invention in this example, are the following:

| Propylene | 84.5% |
|---|---|
| Propane | 93.1% |
| $C_4^+$ ess. | 100.0% |

Calculated process conditions and flow rates are set forth in more detail in the following Table IV:

TABLE IV

| | SIMULATED PROCESS CONDITIONS | | | | | | | |
|---|---|---|---|---|---|---|---|---|
| | STREAM 71 | STREAM 61 | STREAM 62 | STREAM 63 | STREAM 65 | STREAM 66 | STREAM 67 | STREAM 68 |
| Total Moles/hr | 4418 | 251 | 4157 | 300 | 277 | 4134 | 284 | 4134 |
| Pressure, psia | 192 | 190 | 190 | 54 | 54 | 53 | 54 | 53 |
| Temperature | 100 | −46 | −46 | −117 | −61 | −129 | 30 | −102 |
| $H_2$ (Moles/hr) | 781 | 1 | 780 | nil | 1 | 781 | nil | 781 |
| $C_1$ (Moles/hr) | 2277 | 20 | 2257 | 14 | 34 | 2277 | nil | 2277 |
| $C_2$ (Moles/hr) | 933 | 82 | 751 | 135 | 214 | 930 | 2 | 930 |
| $C_3$ (Moles/hr) | 209 | 75 | 134 | 135 | 26 | 24 | 184 | 25 |
| $C_4$ (Moles/hr) | 52 | 39 | 13 | 13 | nil | nil | 52 | nil |

I claim:

1. In a process for separating a hydrocarbon gas containing at least ethane and $C_3$ components into a fraction containing a predominant portion of the ethane and lighter components and a fraction containing a predominant portion of the $C_3$ and heavier components, in which process (a) the feed gas is treated in one or more heat exchangers, and expansion steps to provide at least one partly condensed hydrocarbon gas, providing thereby at least one first residue vapor and at least one $C_3$-containing liquid which liquid also contains lighter hydrocarbons; and (b) at least one of the $C_3$-containing liquids is directed into a distillation column wherein said liquid is separated into a second residue containing lighter hydrocarbons and a $C_3$-containing product;

the improvement comprising (1) cooling said second residue to partially condense it;

(2) intimately contacting at least part of one of said first residue vapors with at least part of the liquid portion of the partially condensed second residue in at least one contacting stage and thereafter separating the vapors and liquids from said contacting stage;

(3) supplying the liquids thereby recovered to the distillation column as a liquid feed thereto; and (4) directing the vapors thereby recovered into heat exchange relation with said second residue from the distillation column, thereby to supply the cooling of step (1), and thereafter discharging said residue gases.

2. The improvement according to claim 1 wherein said contacting step (2) is carried out in a feed separator/absorber which includes fractionation means for vapor/liquid counter-current contact and (i) wherein said partly condensed second residue is introduced into said separator/absorber above said fractionation means, whereby the liquid portion of it passes downwardly through said fractionation means; and (ii) said at least part of one of said first residue vapors is supplied to said separator/absorber below said fractionation means, whereby the first residue vapor rises through said fractionation means in counter-current contact with the liquid portion of the partly condensed second residue.

3. The improvement according to claim 2 wherein the fractionation means in said separator/absorber provide the equivalent of at least one theoretical distillation stage arranged to contact at least part of one of said first residue vapors with the liquid portion of the partly condensed second residue.

4. The improvement according to claim 2 wherein the fractionation means in said separator/absorber provide the equivalent of at least three theoretical distillation stages arranged to contact at least part of one of said first residue vapors with the liquid portion of the partly condensed second residue.

5. The improvement according to claim 1 wherein at least part of one of said first residue vapors are co-mingled with the liquid portion of the partially condensed second residue.

6. The improvement according to claim 1 wherein at least part of one of said first residue vapors and are comingled with both the liquid portion and vapor portion of said partially condensed second residue.

7. In an apparatus for separating a hydrocarbon gas containing at least ethane and $C_3$ components into a fraction containing a predominant portion of ethane and lighter components and a fraction containing a predominant portion of the $C_3$ and heavier components in which apparatus (a) one or more heat exchange means and one or more expansion means are provided which are cooperatively connected to provide at least one partly condensed hydrocarbon gas, providing thereby at least one first residue vapor and at least one $C_3$-containing liquid which liquid also contains lighter hydrocarbons and (b) a distillation column connected to receive at least one of said $C_3$-containing liquids which is adapted to separate the $C_3$-containing liquids into a second residue containing lighter hydrocarbons and a $C_3$-containing product;

the improvement comprising (1) heat exchange means connected to said distillation column to receive said second residue and to partially condense it;

(2) contacting and separating means connected to receive at least part of one of the first residue vapors and at least part of the liquid portion of the partially condensed second residue and to comingle said vapor and liquid in at least one contacting stage, which means include separation means for separating the vapor and liquid after contact in said stage;

(3) said means (2) being further connected to supply the liquids separated therein to the distillation column as a liquid feed thereto, and (4) said means (2) also being connected to direct the vapors separated therein into heat exchange relation with said second residue from the distillation column in said heat exchange means (1).

8. The improvement according to claim 7 wherein said contacting and separating means includes fractionation means for countercurrent vapor/liquid contact and wherein said means is connected to receive the portion of one of first residue vapors to be treated therein below said fractionation means and to receive the portion of said liquids from the partially condensed second residue to be treated therein above said fractionation means said fractionation means thereby being adapted so that the first residue vapors rise therethrough in countercurrent contact with partially condensed second residue.

9. The improvement according to claim 8 wherein said fractionation means includes vapor/liquid contacting means which are the equivalent of at least one theoretical distillation stage.

10. The improvement according to claim 7 wherein said contacting and separating means (2) comprise means for comingling at least part of one of said first residue vapors with the liquid portion of the partially condensed second residue.

11. The improvement according to claim 7 wherein said contacting and separating means (2) comprise means for comingling at least part of one of said first residue vapors with both the liquid and vapor portion of said partially condensed second residue.

* * * * *

UNITED STATES PATENT AND TRADEMARK OFFICE
CERTIFICATE OF CORRECTION

PATENT NO. : 4,617,039

DATED : October 14, 1986

INVENTOR(S) : Loren L. Buck

It is certified that error appears in the above-indentified patent and that said Letters Patent is hereby corrected as shown below:

Col. 7, lines 2-3, "depropanizer" should read --deethanizer--;

Col. 7, line 11, "methane" should read --ethane--;

Col. 7, line 13, "meth-" should read --eth---;

Col. 8, Table II, "stream" should read 32
--stream--.
 31

Signed and Sealed this

Twenty-first Day of January, 1997

Attest:

BRUCE LEHMAN

Attesting Officer

Commissioner of Patents and Trademarks